United States Patent
Kim et al.

(10) Patent No.: US 10,384,044 B2
(45) Date of Patent: Aug. 20, 2019

(54) SINUS BALLOON CATHETER WITH ADJUSTABLE BENDING ANGLE AND BALLOON POSITION

(71) Applicants: GIL MEDICAL CENTER, Incheon (KR); GACHON UNIVERSITY OF INDUSTRY-ACADEMIC COOPERATION FOUNDATION, Seongnam-si (KR)

(72) Inventors: Seontae Kim, Seongnam-si (KR); Hanyong Chun, Goyang-si (KR); Donghyuk Lee, Seoul (KR); Soohwa Song, Incheon (KR)

(73) Assignees: GIL MEDICAL CENTER, Incheon (KR); GACHON UNIVERSITY OF INDUSTRY-ACADEMIC COOPERATION FOUNDATION, Seongnam-si (KR)

( * ) Notice: Subject to any disclaimer, the term of this patent is extended or adjusted under 35 U.S.C. 154(b) by 277 days.

(21) Appl. No.: 15/362,525

(22) Filed: Nov. 28, 2016

(65) Prior Publication Data
US 2018/0147395 A1    May 31, 2018

(30) Foreign Application Priority Data
Nov. 25, 2016    (KR) .................. 10-2016-0158375

(51) Int. Cl.
*A61M 29/02*    (2006.01)
*A61M 25/10*    (2013.01)
(Continued)

(52) U.S. Cl.
CPC ........ *A61M 29/02* (2013.01); *A61M 25/0136* (2013.01); *A61M 25/10182* (2013.11); *A61B 17/24* (2013.01); *A61M 2029/025* (2013.01)

(58) Field of Classification Search
CPC ........ A61M 25/0147; A61M 2025/015; A61M 25/0136; A61M 25/0133; A61M 29/02; A61B 17/24
See application file for complete search history.

(56) References Cited

U.S. PATENT DOCUMENTS 5,766,151 A * 6/1998 Valley .............. A61B 17/00234
                                                          604/103.07
2002/0165485 A1    11/2002 Simpson et al.
(Continued)

FOREIGN PATENT DOCUMENTS

JP    9-28665 A    2/1997
JP    2015-83021 A    4/2015
(Continued)

*Primary Examiner* — Thomas M McEvoy
(74) *Attorney, Agent, or Firm* — Seed IP Law Group LLP

(57) ABSTRACT

Disclosed is a sinus balloon catheter. The sinus balloon catheter includes a body unit, a bending angle adjusting unit that includes a bending angle adjusting lever and a rotary plate, and a guide unit that includes a balloon, and has a pair of bending angle adjusting wires therein. The guide unit includes a first guide body, and a second guide body that is slidably provided in the first guide body, the balloon is provided on the second guide body, the rotary plate is connected to any one of the pair of bending angle adjusting wires to be rotated, and the other bending angle adjusting wire is maintained within the guide unit, and the guide unit is inserted into any one of a sphenoidal sinus, a frontal sinus, and a maxillary sinus.

14 Claims, 7 Drawing Sheets

(51) Int. Cl.
*A61M 25/01* (2006.01)
*A61B 17/24* (2006.01)

(56) References Cited

U.S. PATENT DOCUMENTS

| | | |
|---|---|---|
| 2006/0163436 A1 | 7/2006 | Chandra et al. |
| 2007/0203474 A1 | 8/2007 | Ryan et al. |
| 2010/0241155 A1 | 9/2010 | Chang et al. |
| 2014/0088355 A1 | 3/2014 | Schaeffer |
| 2014/0180328 A1 | 6/2014 | Vaccaro et al. |

FOREIGN PATENT DOCUMENTS

| | | |
|---|---|---|
| KR | 2012-0012796 A | 2/2012 |
| KR | 2015-0113953 A | 10/2015 |
| KR | 2015-0133533 A | 11/2015 |

\* cited by examiner

[FIG. 1]
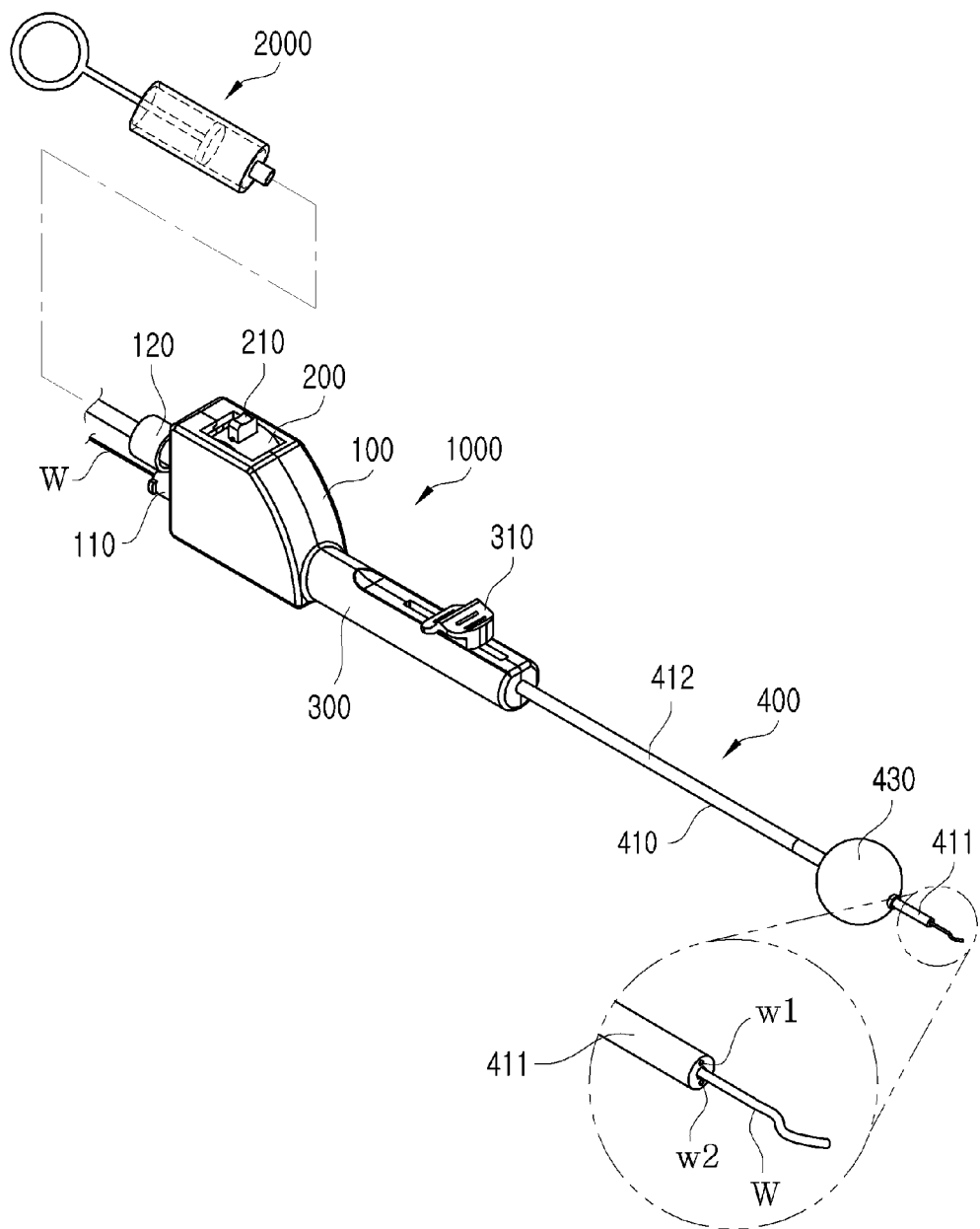

[FIG. 2]
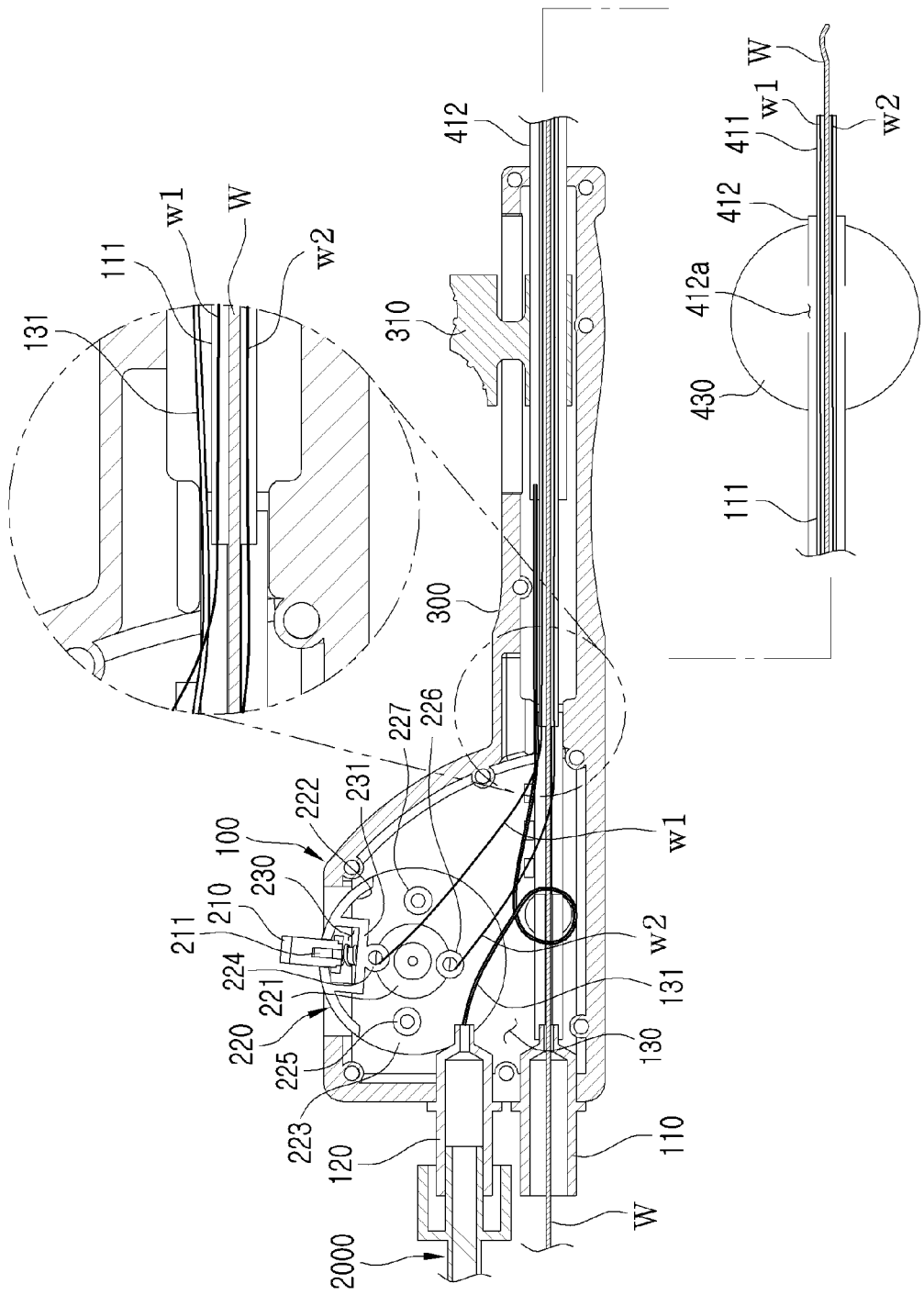

[FIG. 3]
(a)
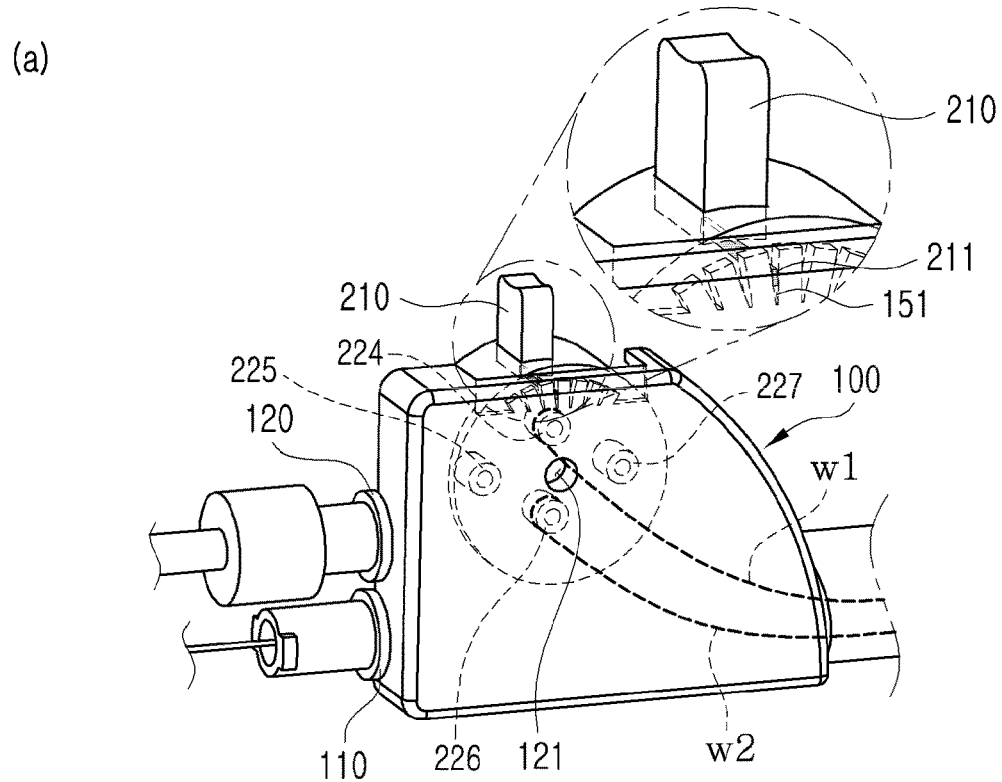
(b)
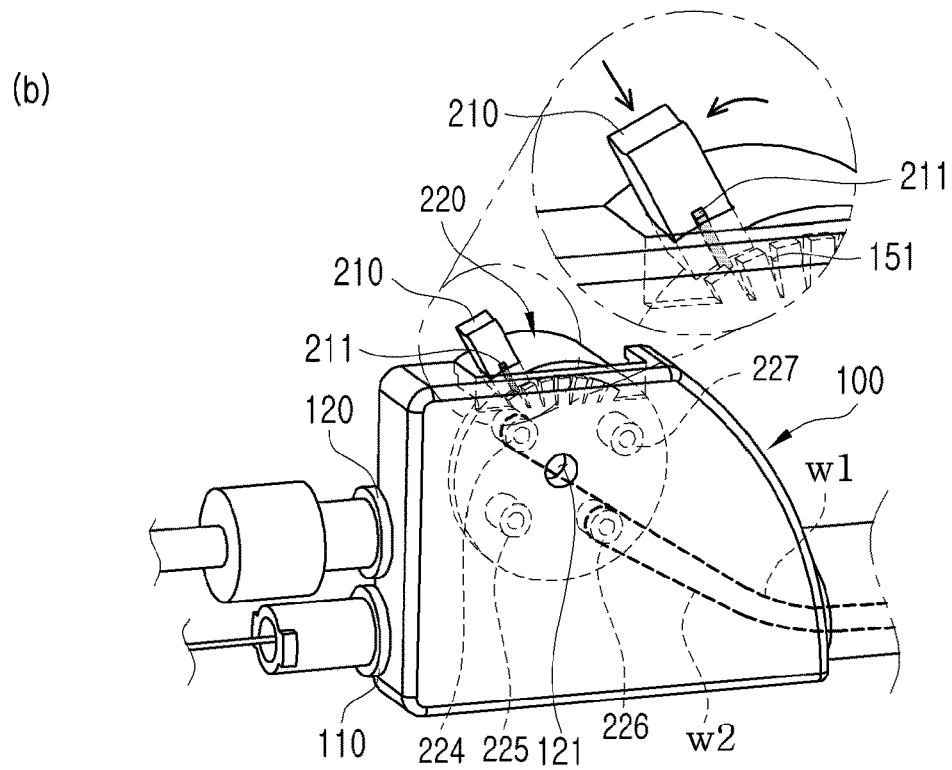

[FIG. 4]
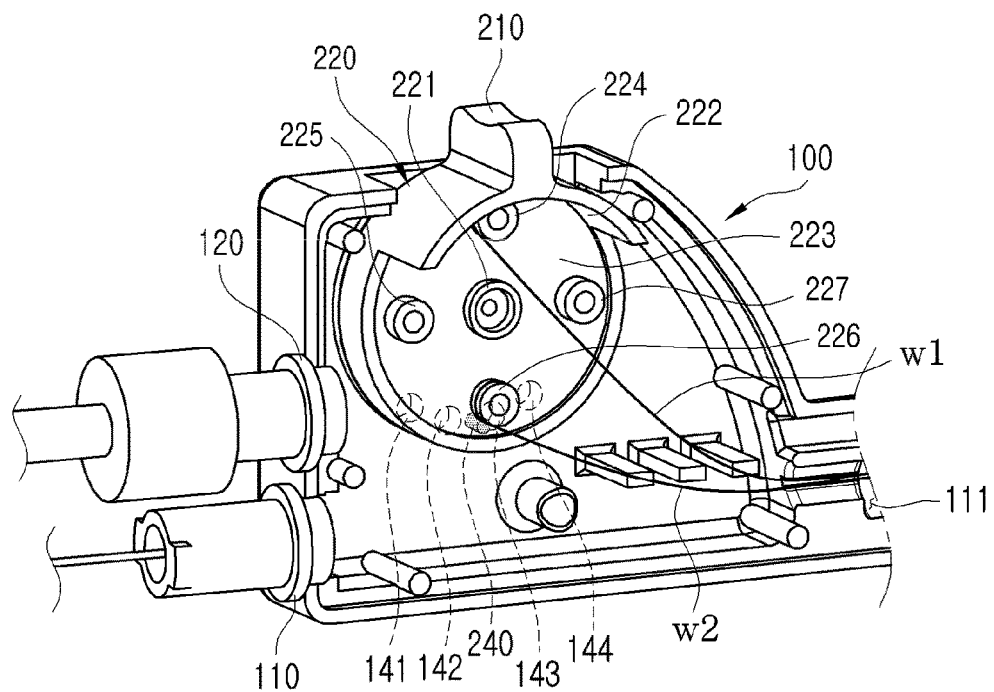

[FIG. 5]
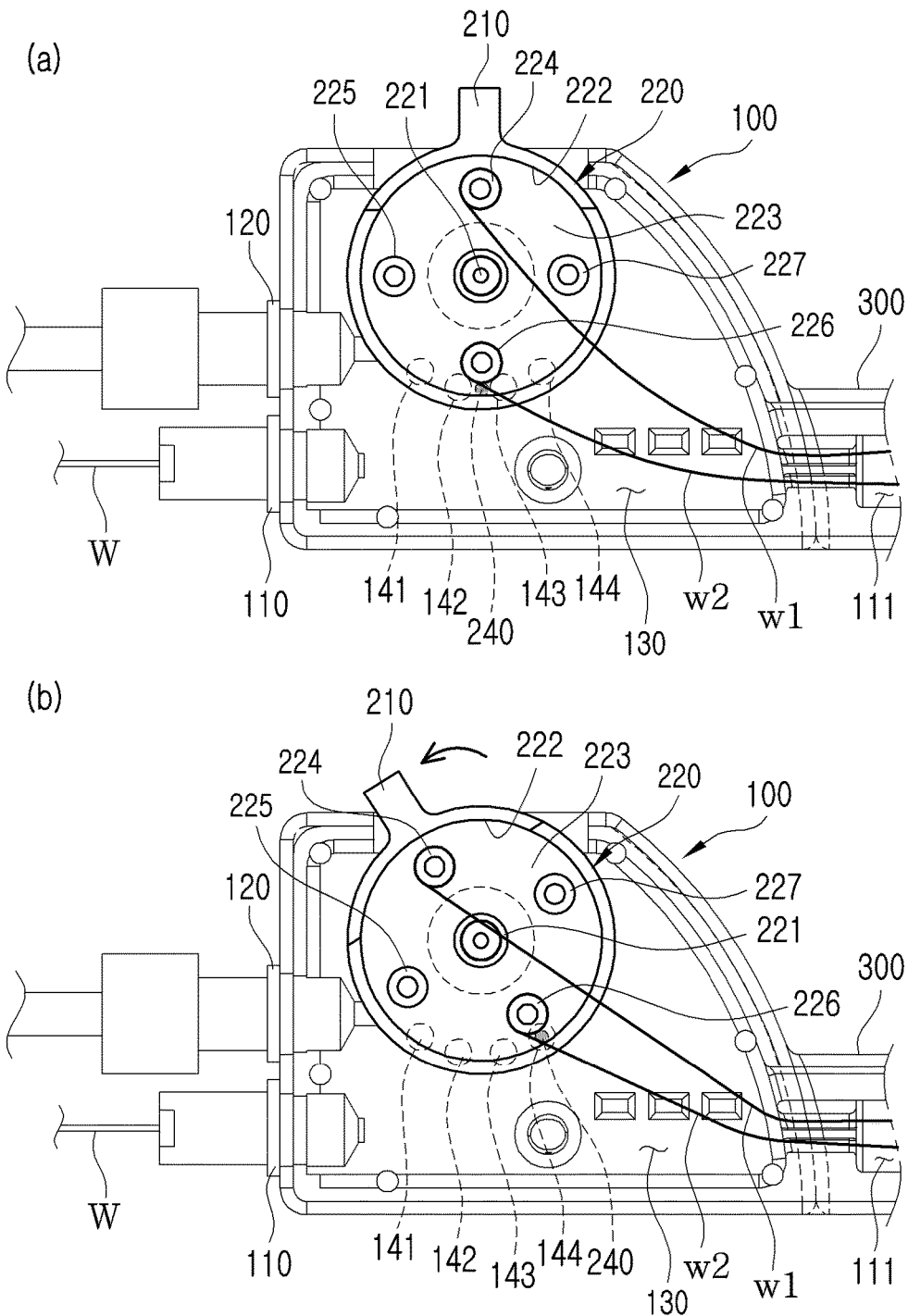

[FIG. 6]
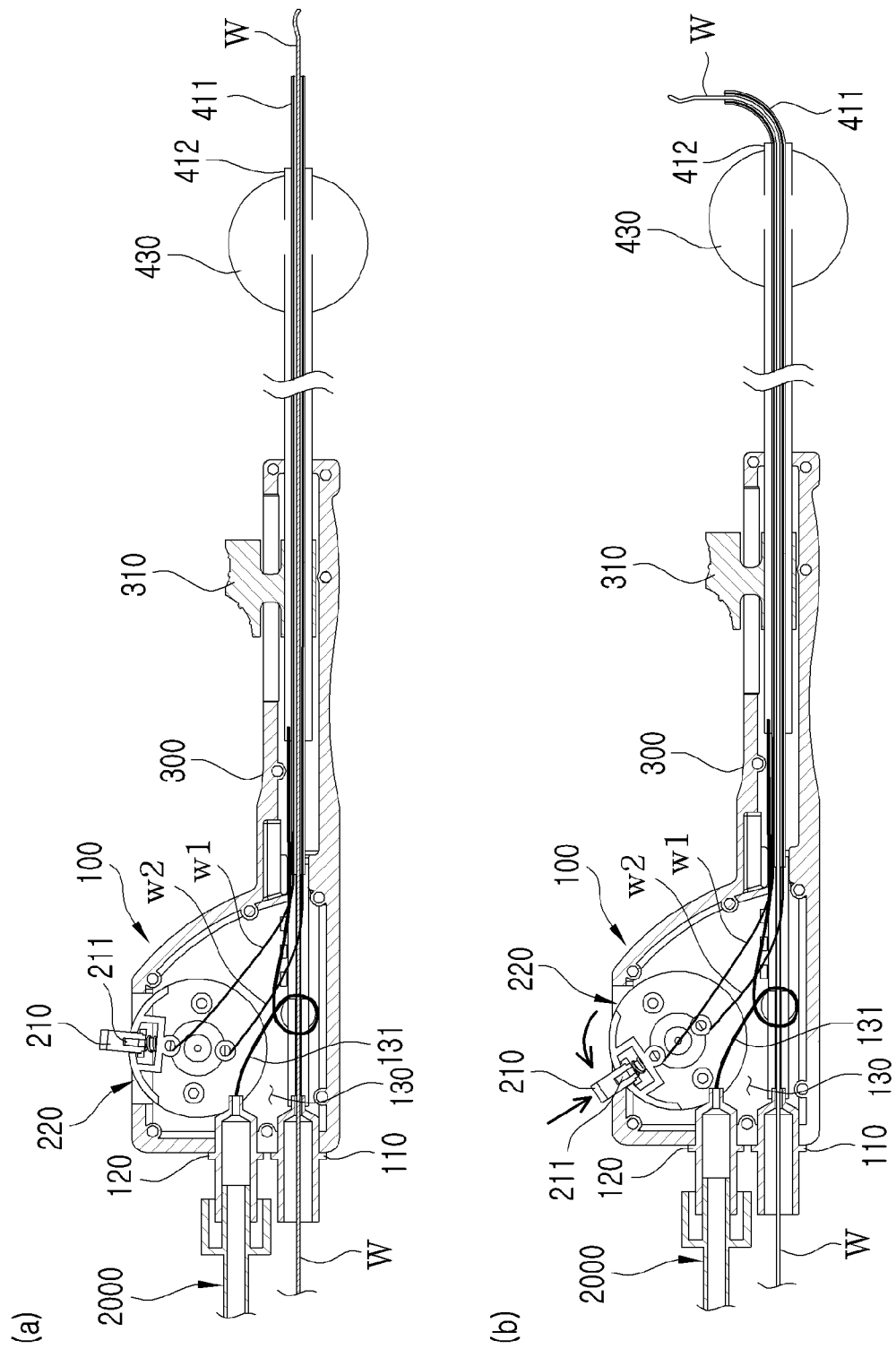

[FIG. 7]
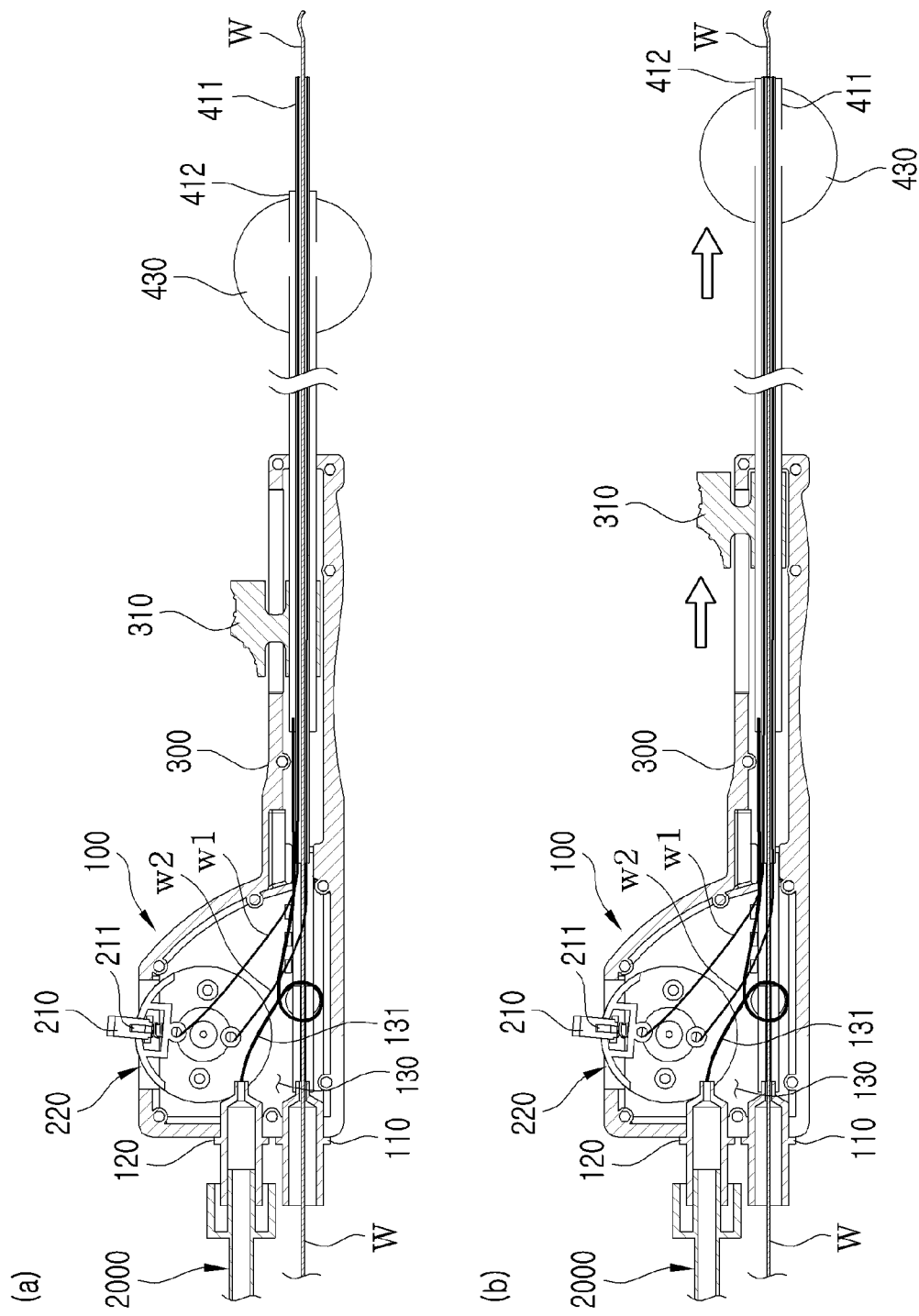

US 10,384,044 B2

SINUS BALLOON CATHETER WITH ADJUSTABLE BENDING ANGLE AND BALLOON POSITION

CROSS-REFERENCE TO RELATED APPLICATION

This application claims priority from and the benefit under 35 U.S.C. § 119(a) of Korean Patent Application No. 10-2016-0158375, filed on Nov. 25, 2016, which is hereby incorporated by reference for all purposes as if fully set forth herein.

BACKGROUND OF THE INVENTION

1. Field of the Invention

The present invention relates to a balloon catheter, and more particularly, to a balloon catheter in which a bending angle of a tip end thereof and a position of a balloon may be freely adjusted.

2. Description of the Prior Art

Sinusitis is a disease by which secretion of a sinus cannot be easily discharged due to an abnormality of the sinus so that germ infection and inflammation are caused, a mucous membrane is swollen, and an entrance of the sinus is narrowed. It is often called sinus infection, and causes severe inconvenience to the daily life of the patient.

A surgical procedure method using a balloon catheter as a method for treating sinusitis rapidly recovers a cutaway portion of the patient as compared with an existing surgical procedure method. The balloon catheter surgical procedure is performed by inserting a catheter into a nasal cavity of the patient, expanding an entrance of the sinus by expanding a balloon situated at a distal end of the catheter, and removing inflammation and secretion in the sinus.

The sinus includes a frontal sinus, a maxillary sinus, and a sphenoidal sinus, and a balloon catheter having a bending angle corresponding to the portion is necessary in order to insert the balloon catheter.

Accordingly, Korean Patent Application Publication No. 10-2015-0113953 discloses a catheter a sinus expanding device that includes a frontal sinus expanding device, a maxillary sinus expanding device, and a sphenoidal sinus expanding device, but it relates to a catheter having a fixed bending angle and fails to adjust a bending angle of a balloon catheter.

Korean Patent Application Publication No. 10-2012-0012796 discloses a technology of inclining catheter at an angle of 0 to 180 degrees with respect to a shaft through a flexible distal tip, but the catheter is inclined simply due to the flexible distal tip and a bending angle of the balloon catheter cannot be adjusted.

SUMMARY OF THE INVENTION

The present invention has been made in an effort to solve the above-mentioned problems.

In particular, the present invention provides a sinus balloon catheter that may be inserted according to the sinus structures that are different for the patients by freely adjusting a bending angle of the balloon catheter and a position of a balloon.

In accordance with an aspect of the present invention, there is provided a sinus balloon catheter including a body unit, a bending angle adjusting unit that includes a bending angle adjusting lever and a rotary plate, and a guide unit that includes a balloon, and has a pair of bending angle adjusting wires therein, wherein the guide unit includes a first guide body, and a second guide body that is slidably provided in the first guide body, the balloon is provided on the second guide body, the rotary plate is connected to any one of the pair of bending angle adjusting wires to be rotated, and the other bending angle adjusting wire is maintained within the guide unit, and the guide unit is inserted into any one of a sphenoidal sinus, a frontal sinus, and a maxillary sinus.

According to an embodiment, a bending angle of a tip end of the guide unit may be adjusted through rotation of the rotary plate.

According to an embodiment, the body unit may include a fluid injection part, and the sinus balloon catheter may further include a fluid injection unit that is connected to the fluid injection part to inject a fluid into the balloon.

According to an embodiment, the bending angle adjusting lever may protrude to the outside of the body unit, and the rotary plate may be connected to the pair of bending angle adjusting wires while being rotated by the bending angle adjusting lever.

According to an embodiment, the rotary plate may have a disk shape.

According to an embodiment, the rotary plate may be provided with a mounting rod that protrudes from the rotary plate, and a mounting hole, into which the mounting rod is inserted, may be formed in the body unit.

According to an embodiment, the rotary plate may be rotatable about the mounting rod while the mounting rod is inserted in the mounting hole.

According to an embodiment, the rotary plate may include a plurality of rotation rods that are arranged around the mounting rod, and any one of the pair of bending angle adjusting wires may be connected to any one of the plurality of rotation rods.

According to an embodiment, the rotary plate may include a curved surface, into which the bending angle adjusting lever is inserted to be mounted on the curved surface, and a flat side surface that is perpendicular to the curved surface.

According to an embodiment, a lever mounting chamber, in which the bending angle adjusting lever is mounted, may be formed on the curved surface, and the bending angle adjusting lever may be mounted on a bottom surface of the lever mounting chamber by a resilient member.

According to an embodiment, a fixing protrusion for fixing the bending angle of the guide unit may be mounted at a lower end of the bending angle adjusting lever, and at least one fixing hole, into which the fixing protrusion is inserted, may be formed on an upper surface of the body unit.

According to an embodiment, a first magnetic groove, in which a first magnetic body having a first polarity is mounted, may be formed on a side surface of the rotary plate, and a plurality of second magnetic grooves, in which second magnetic bodies having a second polarity that is opposite to the first polarity are mounted, may be formed on a side surface of the body unit that faces a side surface of the rotary plate.

According to an embodiment, the first magnetic groove may be aligned with any one of the plurality of second magnetic grooves through rotation of the rotary plate.

According to an embodiment, the sinus balloon catheter further include an extension part that extends from a tip end of the body unit to surround the guide unit, and a balloon position adjusting lever for sliding of the second guide body may be formed in the extension part.

According to an embodiment, a fluid injection groove for injecting a fluid into the balloon may be formed in the second guide body.

BRIEF DESCRIPTION OF THE DRAWINGS

The above and other objects, features and advantages of the present invention will be more apparent from the following detailed description in conjunction with the accompanying drawings, in which:

FIG. 1 is a perspective view of a sinus balloon catheter according to an embodiment of the present invention;

FIG. 2 is a longitudinal sectional view of the sinus balloon catheter of FIG. 1;

FIG. 3 is a view illustrating a body unit and a bending angle adjusting unit for a sinus balloon catheter according to a first embodiment of the present invention;

FIG. 4 is a view illustrating a body unit and a bending angle adjusting unit for a sinus balloon catheter according to a second embodiment of the present invention;

FIG. 5 is a view for explaining an operation of the sinus balloon catheter of FIG. 4;

FIG. 6 is a view for explaining an operation of adjusting a bending angle of the sinus balloon catheter of FIG. 1; and FIG. 7 is a view for explaining an operation of adjusting a position of a balloon of the sinus balloon catheter of FIG. 1.

DETAILED DESCRIPTION OF THE EXEMPLARY EMBODIMENTS

First, a sinus balloon catheter of the present invention will be described in detail with reference to the accompanying drawings. It is described in advance that the balloon of the sinus balloon catheter illustrated in the drawings is expanded through injection of a fluid.

1. First Embodiment

First, the sinus balloon catheter according to a first embodiment of the present invention will be described with reference to FIGS. 1 to 3.

Referring to FIG. 1, the sinus balloon catheter according to the first embodiment of the present invention includes a balloon catheter body 1000 and a fluid injection unit 2000.

The balloon catheter body 1000 is a part that is inserted into a sinus to perform a treatment. Referring to FIG. 1, the balloon catheter body 1000 includes a body unit 100, a bending angle adjusting unit 200, an extension part 300, and a guide unit 400.

The body unit 100 is a part, to which the bending angle adjusting unit 200 for adjusting a bending angle of the balloon catheter is mounted. The body unit 100 includes a guide wire insertion part 110 and a fluid injection part 120.

A plurality of fixing grooves 141 for fixing a bending angle of the balloon catheter are formed on an upper surface of the body unit 100. A fixing protrusion 211, which will be described below, is inserted into any one of the plurality of fixing grooves 141 to prevent movement of the bending angle adjusting lever 210.

The guide wire insertion part 110 is situated at a rear end of the body unit 100 such that a guide wire W is inserted through a guide channel 111. It is preferable that the length of the guide wire W is longer than sum of the length of the body unit 100, the extension part 300, and the guide unit 400. In this case, the guide wire W may protrude to the outside of the guide unit 400. The guide wire W that protrudes to the outside guides insertion of the balloon catheter into the sinus. Further, a lighting function, for example, of an LED lamp, may be provided at a distal end of the guide wire W. Accordingly, it may be identified whether the balloon catheter is inserted into the sinus at a proper position, by identifying light of an outside (a brow or a cheekbone) of a face, which is emitted by the LED lamp Like the guide wire insertion part 110, the fluid injection part 120 is situated at a rear end of the body unit 100. A fluid injection unit 2000 is connected to the fluid injection part 120. When the user injects a fluid through the fluid injection unit 2000, the fluid is injected into the balloon 430 through the fluid injection channel 131 such that the balloon 430 is expanded. A distal end of the fluid injection channel 131 is connected to a second guide body 412 such that the fluid may be injected into the balloon 430 through the fluid injection groove 412a. The balloon 430 is expanded through injection of the fluid to widen an entrance of the sinus that has been narrowed by inflammation.

The bending angle adjusting unit 200 is a part that is mounted on a mounting chamber 130 of the body unit 100 and is connected to bending angle adjusting wires w1 and w2 to adjust a bending angle of a tip end of the balloon catheter. Here, a bending angle refers to a degree by which the tip end of the balloon catheter is inclined with respect to the guide unit 400. It is preferable that a bending angle of the tip end of the balloon catheter be freely adjusted by the bending angle adjusting unit 200, and be adjusted such that the balloon catheter may be inserted into at least one of a sphenoidal sinus, a frontal sinus, and a maxillary sinus. Referring to FIGS. 2 to 4, the bending angle adjusting unit 200 includes a bending angle adjusting lever 210, a rotary plate 220, and a lever mounting chamber 230.

The bending angle adjusting lever 210 is a part that protrudes to the outside of the body unit 100, and is inserted into the rotary plate 220. The user may rotate the rotary plate 220 by manipulating the bending angle adjusting lever 210, and may adjust a bending angle of the catheter by adjusting the bending angle adjusting wires w1 and w2 connected to the rotary plate 220.

A fixing protrusion 211 for fixing a bending angle of the balloon catheter is mounted at a lower end of the bending angle adjusting lever 210. It is preferable that bending angles that are suitable for the angles of sinuses, which have been determined based on a general anatomic structure be marked on a surface of the body unit 100. The bending angle of the tip end of the balloon catheter may be adjusted and then fixed such that the balloon catheter may be easily inserted into portions of the sinuses through the angles marked on the body unit 100. It is apparent that the bending angle of the tip end of the balloon catheter may be minutely adjusted and then fixed based on the individually different structures of the sinuses.

Referring to FIG. 3, the bending angle of the balloon catheter may be adjusted as the user presses the bending angle adjusting lever 210. In more detail, when no force is applied to the bending angle adjusting lever 210, the fixing protrusion 211 continues to be inserted in the fixing groove 141 (FIG. 3A). The fixing protrusion 211 is not moved even if a force is applied to the bending angle adjusting lever 210, and the bending angle of the balloon catheter is also fixed.

When a force is applied to the bending angle adjusting lever 210, the fixing protrusion 211 mounted on the bending angle adjusting lever 210 is rotated about a surface of the fixing protrusion 211, on which the bending angle adjusting lever 210 is mounted, and is separated from the fixing groove 141 (FIG. 3B) The bending angle adjusting lever 210 may be moved, and if the bending angle adjusting lever 210 is moved forwards and rearwards, the bending angle of the balloon catheter may be adjusted.

The rotary plate 220 is a part that is rotated through motion of the bending angle adjusting lever 210.

It is preferable that the rotary plate 220 has a disk shape. It is preferable that a protruding mounting rod 221 be provided at the center of the rotary plate 220, and a mounting hole 121, into which the mounting rod 221 is inserted, be formed in the body unit 100. If the mounting rod 221 is inserted into the mounting hole 121, the bending angle adjusting unit 200 is mounted on the body unit 100. The rotary plate 220 of the bending angle adjusting unit 200 is rotated about the mounting rod 211 while the mounting rod 221 is inserted in the mounting hole 121.

Referring to FIG. 2, the rotary plate 220 includes a curved surface 222, on which the bending angle adjusting lever 210 is mounted, and a flat side surface 223 that is perpendicular to the curved surface 222.

A lever mounting chamber 230, in which the bending angle adjusting lever 210 is mounted, is formed at a lower end of the curved surface 222. The bending angle adjusting lever 210 is mounted on a bottom surface 231 of the lever mounting chamber 230 by a resilient member 232.

A plurality of rotation rods 224, 225, 226, and 227 that are arranged around the mounting rod 221 protrude from the side surface 223 of the rotary plate 220. Any one of the bending angle adjusting wires w1 and w2 is connected to any one of the plurality of rotation rods 224, 225, 226, and 227. If the rotary plate 220 is rotated, the plurality of rotation rods 224, 225, 226, and 227 are rotated together and the bending angle adjusting wires w1 and w2 connected to the rotation rods are also moved. Accordingly, the bending angle of the tip end of the balloon catheter including the bending angle adjusting wires w1 and w2 may be adjusted.

The extension part 300 extends from the tip end of the body unit 100 to surround the guide body 410.

A balloon position adjusting lever 310 for sliding of the second guide body 412 is formed in the extension part 300. The balloon position adjusting lever 310 surrounds the second guide body 412. The balloon position adjusting lever 310 allow the second guide body 412 to be slid while moving forwards and rearwards through a sliding groove 311.

The guide unit 400 is a part that is inserted into a sinus. Referring to FIGS. 1 and 2, the guide unit 400 includes a guide body 410 and a balloon 430.

The guide body 410 includes a first guide body 411 and a second guide body 412.

A guide channel 111 penetrates longitudinally in the first guide body 411. The guide channel 111 is a passage, into which the guide wire W is inserted. The guide wire W passes through the guide channel 111 and protrudes to the outside of the guide unit 400 to guide the insertion of the guide unit 400 into the sinus.

A pair of bending angle adjusting wires w1 and w2 are provided within the first guide body 411. It is preferable that the bending angle adjusting wires have a maximum spacing distance within the first guide body 411 such that the bending angle of the first guide body 411 may be easily adjusted.

The bending angle adjusting wires w1 and w2 adjust a bending angle of the tip end of the guide body 410 through a change of the shapes thereof within the guide body 410. The number of the bending angle adjusting wires is not limited, and it will be described as an example that the number of the bending angle adjusting wires w1 and w2 is two.

Referring to FIG. 2, the first bending angle adjusting wire w1 is connected to a first rotation rod 224, and the second bending angle adjusting wire w2 is connected to a third rotation rod 226. Because the rotation rods are also rotated as the rotary plate 220 is rotated, the shape of any one of the first bending angle adjusting wire w1 and the second bending angle adjusting wire w2 that are connected to the rotation rods changes.

It is preferable that the tip end of the first guide body 411 be formed of a flexible tube. Accordingly, if the shapes of the first bending angle adjusting wire w1 and the second bending angle adjusting wire w2 change, the tube of the flexible material may be deformed according to the change of the shapes of the bending angle adjusting wires (FIG. 6).

The second guide body 412 has a diameter that is larger than that of the first guide body 411, and surrounds the first guide body 411. It is preferable that the second guide body 412 is slidably provided in the first guide body 411. The second guide body 412 may be slid through manipulation of the balloon position adjusting lever 310 that surrounds the second guide body 412.

The balloon 430 is a part that is expanded if a fluid is injected into the balloon 430 by the fluid injection unit 2000 to widen the entrance of the sinus, which has been narrowed by inflammation. The balloon 430 is provided on the second guide body 412 and is moved together with the second guide body 412 when the second guide body 412 is slid. That is, the position of the balloon 430 may be adjusted through manipulation of the balloon position adjusting lever 310.

A fluid injection groove 412a for injecting a fluid is formed in the second guide body 412. When the fluid is injected by the fluid injection unit 2000, the fluid reaches the balloon 430 via the fluid injection channel 131, the second guide body 412, and the fluid injection groove 412a.

2. Second Embodiment

Hereinafter, the sinus balloon catheter according to a second embodiment of the present invention will be described with reference to FIGS. 4 to 5.

As in the first embodiment, a bending angle of the tip end of the balloon catheter is adjusted through manipulation of the bending angle adjusting unit 200, and the position of the balloon 430 is changed through manipulation of the balloon position adjusting lever 310.

However, as a configuration of fixing the bending angle of the balloon catheter is different from that of the first embodiment, a description of the same parts will be omitted and only parts that are different from those of the first embodiment will be described in detail.

Referring to FIG. 4, a first magnetic groove 240, into which a first magnetic body having a first polarity is inserted, is formed on a side surface 223 of the rotary plate 220. A plurality of second magnetic grooves 141, 142, 143, and 144, into which a second magnetic body having a second polarity that is opposite to the first polarity is inserted, are formed on a side surface of the body unit 100, which the side surface 223 of the rotary plate 220 faces.

Here, the first polarity may be N pole, and the second polarity may be S pole.

However, the present invention is not limited thereto, and materials that may apply an attractive force may be arbitrarily used.

If the rotary plate 220 is rotated through manipulation of the bending angle adjusting lever 210, the first magnetic groove 240 formed in the rotary plate 220 is aligned with any one of the plurality of second magnetic grooves 141, 142, 143, and 144 (FIG. 5B). As the first magnetic body inserted into the first magnetic groove 240 and the second magnetic bodies inserted into the second magnetic grooves 141, 142, 143, and 144 have opposite polarities, they are coupled to each other due to the attractive forces.

In the sinus catheter according to the second embodiment, the bending angle of the tip end of the balloon catheter may be fixed by coupling the first magnetic body and the second magnetic bodies.

According to the present invention, because the bending angle of the tip end of the balloon catheter may be freely adjusted, the balloon catheter may be easily inserted into various portions of the sinus.

Because the position of the balloon provided in the balloon catheter may be freely adjusted, the precision of the surgical procedure may be improved.

The time for the surgical procedure may be reduced by easily changing the bending angle of the tip end of the catheter according to the portion of the sinus, which is to be treated, and manufacturing costs of the balloon catheter and surgery costs may be reduced because the distal tip may be variously manufactured and a separate device is not necessary.

Although the embodiment of the present invention illustrated in the drawings has been described so that those skilled in the art can easily reproduce and implement the present invention, it is merely exemplary and it will be understood by those skilled in the art that various modifications and equivalent embodiments can be made. Therefore, the scope of the present invention should be determined according to the claims.

What is claimed is:

1. A sinus balloon catheter comprising:
   a body unit;
   a bending angle adjusting unit that comprises a bending angle adjusting lever and a rotary plate;
   a guide unit that comprises a guide channel in which a guide wire is arranged,
   a first guide body with a pair of bending angle adjusting wires, a second guide body that is slidable along the first guide body, and a balloon that is provided on the second guide body; and
   an extension that extends from a tip end of the body unit and encompasses a portion of the guide unit,
   wherein a balloon position adjusting lever, that encompasses the second guide body and adjusts the sliding of the second guide body along the first guide body, is formed in the extension;
   wherein the rotary plate is connected to any one of the pair of bending angle adjusting wires to be rotated, and at least a portion of each of the pair of bending angle adjusting wires is maintained within the first guide body, and
   wherein the guide unit is configured to be inserted into any one of a sphenoidal sinus, a frontal sinus, and a maxillary sinus.

2. The sinus balloon catheter of claim 1, wherein a bending angle of a tip end of the guide unit is adjusted through rotation of the rotary plate.

3. The sinus balloon catheter of claim 1, wherein the body unit comprises a fluid injection part, and the sinus balloon catheter further comprises a fluid injection unit that is connected to the fluid injection part to inject a fluid into the balloon.

4. The sinus balloon catheter of claim 2, wherein the bending angle adjusting lever protrudes to the outside of the body unit, and the rotary plate is connected to the pair of bending angle adjusting wires while being rotated by the bending angle adjusting lever.

5. The sinus balloon catheter of claim 4, wherein the rotary plate has a disk shape.

6. The sinus balloon catheter of claim 5, wherein the rotary plate is provided with a mounting rod that protrudes from the rotary plate, and a mounting hole, into which the mounting rod is inserted, is formed in the body unit.

7. The sinus balloon catheter of claim 6, wherein the rotary plate is rotatable about the mounting rod while the mounting rod is inserted in the mounting hole.

8. The sinus balloon catheter of claim 7, wherein the rotary plate comprises a plurality of rotation rods that are arranged around the mounting rod, and any one of the pair of bending angle adjusting wires is connected to any one of the plurality of rotation rods.

9. The sinus balloon catheter of claim 8, wherein the rotary plate comprises:
   a curved surface, into which the bending angle adjusting lever is inserted to be mounted on the curved surface; and
   a flat side surface that is perpendicular to the curved surface.

10. The sinus balloon catheter of claim 9, wherein a lever mounting chamber, in which the bending angle adjusting lever is mounted, is formed on the curved surface, and the bending angle adjusting lever is mounted on a bottom surface of the lever mounting chamber by a resilient member.

11. The sinus balloon catheter of claim 9, wherein a fixing protrusion for fixing the bending angle of the guide unit is mounted at a lower end of the bending angle adjusting lever, and at least one fixing groove, into which the fixing protrusion is inserted, is formed on an upper surface of the body unit.

12. The sinus balloon catheter of claim 9, wherein a first magnetic groove, in which a first magnetic body having a first polarity is mounted, is formed on a side surface of the rotary plate, and a plurality of second magnetic grooves, in which second magnetic bodies having a second polarity that is opposite to the first polarity are mounted, are formed on a side surface of the body unit that faces a side surface of the rotary plate.

13. The sinus balloon catheter of claim 12, wherein the first magnetic groove is aligned with any one of the plurality of second magnetic grooves through rotation of the rotary plate.

14. The sinus balloon catheter of claim 1, wherein a fluid injection groove for injecting a fluid into the balloon is formed in the second guide body.

* * * * *